United States Patent [19]

Clyne

[11] 4,154,794
[45] May 15, 1979

[54] GAS DETECTOR

[76] Inventor: Arthur J. Clyne, 5651 N. Luce Rd., Alma, Mich. 48801

[21] Appl. No.: 784,986

[22] Filed: Apr. 6, 1977

[51] Int. Cl.² .................... G01N 1/24; G01N 21/06
[52] U.S. Cl. .................... 422/86; 222/209; 422/88
[58] Field of Search ............ 23/254 R, 232 R, 255 R, 23/292; 222/209, 212; 128/145.7

[56] References Cited

U.S. PATENT DOCUMENTS

| | | | |
|---|---|---|---|
| 2,569,895 | 10/1951 | Main-Smith et al. | 23/254 R |
| 2,795,245 | 6/1957 | Meehan | 222/209 X |
| 2,898,007 | 8/1959 | Gassaway | 222/212 |
| 3,356,100 | 12/1967 | Seeler | 128/145.7 X |

FOREIGN PATENT DOCUMENTS 1238650  7/1971  United Kingdom ............ 128/145.7

*Primary Examiner*—R. E. Serwin
*Attorney, Agent, or Firm*—Griffin, Branigan and Butler

[57] ABSTRACT

A hand held gas detector comprises a flexible, transparent, resilient container provided with inlet and outlet valves at opposing ends for controlling flow through inlet and outlet ports, the valves being controlled by the pressure within the container relative to the ambient pressure so that one valve is closed as the other is opened. The container is partially filled with a detector fluid which changes color upon being contacted by the gas being tested for. The container is repetitively squeezed and released to alternately draw ambient atmosphere through the inlet valve into the detector fluid, and exhaust gases in the container back into the atmosphere. The detector liquid returns to its original color in the absence of contact with the gas being detected, hence the device is reusable. The outlet port is located in a downwardly-extending tube which terminates at an opening near the center of the container, so that the detector liquid cannot be ejected through the outlet port even though the container is tilted from its normal upright position of use.

8 Claims, 2 Drawing Figures

GAS DETECTOR

BACKGROUND OF THE INVENTION

Present day conditions have created a need for a very simple and economical test device which an untrained member of the general public may utilize to test for toxic substances in the air he breathes. For example, in certain parts of the country many deaths have occurred in automoblies during recent blizzard conditions with many of these deaths being caused by carbon monoxide poisoning. In addition, the current need for energy conservation has created a potentially hazardous condition in many homes where the home owner has installed energy conservation devices. These devices are often inserted in the furnace flue and recirculate potentially toxic gases.

While many devices exist for measuring or detecting gases or other toxic materials in the atmosphere, most of these devices are so expensive or so complex in operation that their use by the general public has been quite limited.

SUMMARY OF THE INVENTION

An object of the present invention is to provide an inexpensive device which is extremely simple to operate and which will detect the presence of gases or other matter suspended in air or gaseous mixtures.

An object of the present invention is to provide a detector for detecting gases or other matter suspended in air, said detector being portable and manually operable merely by manually squeezing and releasing the device with the fingers of one hand.

A further object of the invention is to provide a detector comprising a flexible, transparent, resilient container having inlet and outlet valves at opposing ends for controlling flow through inlet and outlet ports, the valves being controlled by the pressure within the container relative to ambient pressure so that one valve is closed as the other is opened, the container being partially filled with a detector liquid which changes color upon being contacted by the material being tested for.

A further object of the invention is to provide a detector device which may also be used as a vaporizing device, said device comprising a container for holding a liquid, the container being flexible and resilient and whereby it may be alternately squeezed and released to alternately decrease and increase its internal volume, means defining inlet and outlet ports into and out of the container, the outlet port being located above the level of the liquid and the inlet port being located below the top surface of the liquid, and inlet and outlet valves for controlling the inlet and outlet ports in response to variations in the relative pressures within and without the container, the pressures within and without the container acting on the inlet and outlet valves to open the inlet valve and close the outlet valve when the pressure within the container is less than the pressure without, and to close the inlet valve and open the outlet valve when the pressure within the container is greater than the pressure without.

A further object of the invention is to provide a device as described above wherein the liquid within the container is a detector liquid which changes color upon being brought into contact with a specified substance, the container being made of a transparent plastic material whereby the color of the liquid may be viewed from the exterior of the container.

A further object of the invention is to provide a device as described above wherein a hollow tube extends through one wall of the container and terminates at an opening above the level of the liquid near the central portion of the interior of the container, the outlet port being located at the other end of the tube whereby the container may be tipped from the vertical position of normal use withou permitting the liquid to spill out through the outlet port.

A further object of the invention is to provide a device as described above made entirely of plastic and wherein the valves are plastic flap valves and are hingedly connected to the container by plastic hinge means.

Yet another object of the invention is to provide a valved container as described above wherein the liquid disposed therein is a liquid which vaporizes when air is bubbled therethrough whereby the device may be utilized as a manually operated vaporizer.

Other objects of the invention and its mode of operation will become apparent upon consideration of the following description and the accompanying drawings.

DESCRIPTION OF A PREFERRED EMBODIMENT

Figure 1:
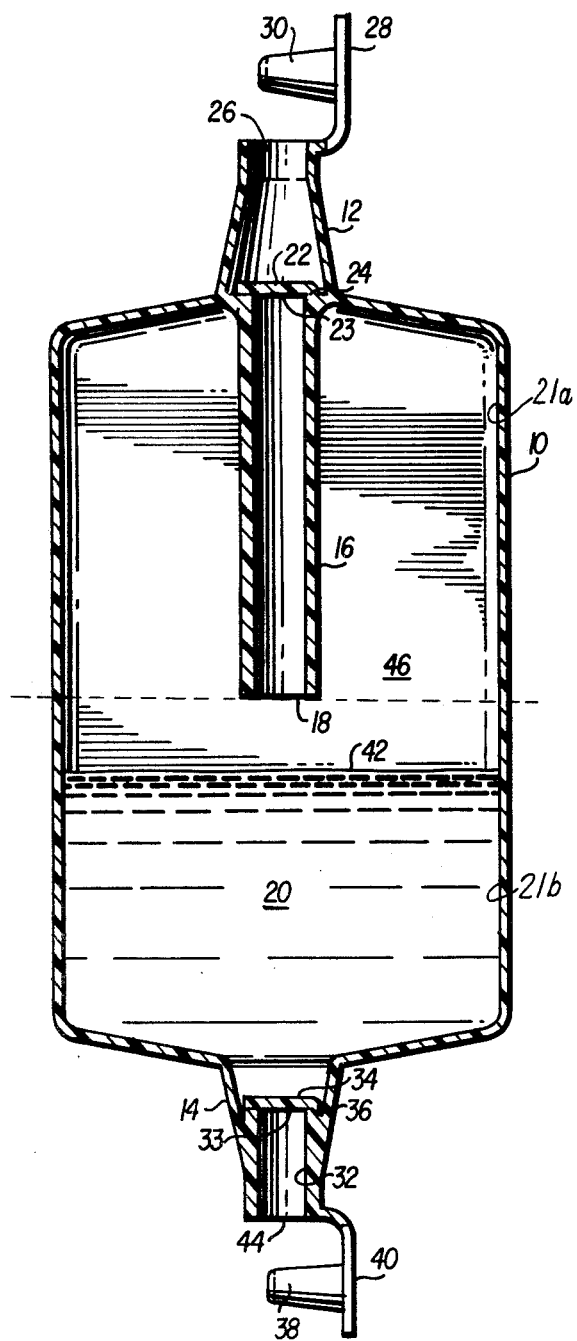
FIG. 1 is a front sectional view of a device constructed in accordance with the principles of the present invention.
Figure 2:
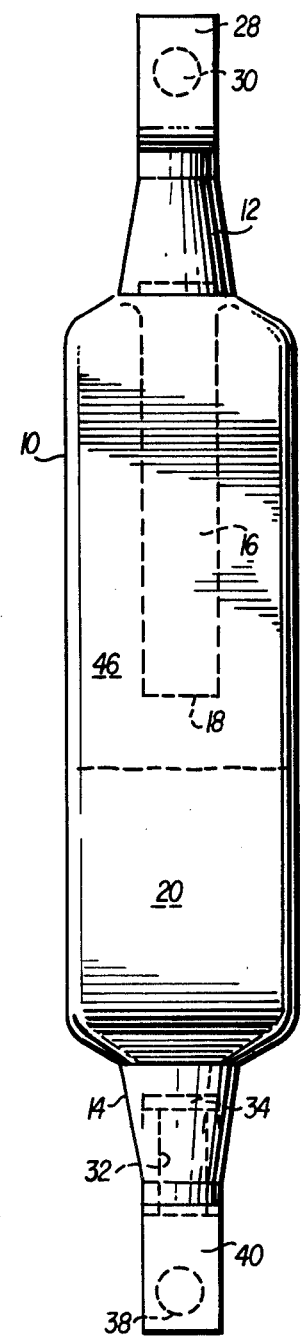
FIG. 2 is a right side view of FIG. 1.

As shown in FIGS. 1 and 2, a gas detector constructed in accordance with the principles of the present invention comprises a container 10 having first and second neck portions 12 and 14. The container may generally be rectangular in shape and preferably has a thickness dimension less than the width or length so that opposing sides of the container may be grasped in one hand between the thumb and fingers. Housing 10 is made of a clear, resilient, transparent plastic material such as polypropylene, for example. A container made of this material is resilient enough to be compressed or squeezed by the hand of the user and still return to its original shape when the user relaxes his grip.

A hollow elongated tube 16 extends through the upper wall of container 10 and extends downwardly until it terminates at an opening 18 in the central portion of the interior of the container. As subsequently described, the container 10 is filled with a liquid 20 and the opening 18 is located above the top surface of the liquid. This enables the container 10 to be tilted from the vertical position without the liquid 20 flowing out of the container through the tube 16. The upper end of tube 16 terminates at a container outlet port 23. In this respect, as can be seen in FIG. 1, the container 10 forms a cavity having a first portion 21a positioned above the opening 18 and a second portion 21b positioned below the opening 18. The volumes of both of these portions, external of the tube 16, are sufficiently great that identical portions of the detector liquid 20, when in the container 10, with the neck portion 14 directed downwardly easily enter into the neck portion 14 thereby contacting and covering a valve 34 which is described below. Ideally, the first and second cavity portions 21a and 21b are approximately equal in size.

An outlet valve 22 covers the outlet port 23 and is located in the neck portion 12. Preferably, valve 22 is a plastic flap valve hingedly connected to the tube 16 by a plastic hinge means 24.

Neck portion 12 is generally hollow and has an opening 26 in its top surface. A plastic cap member 28 is hingedly connected to neck portion 12 by a plastic hinge and has a stopper member 30 which may be placed into the opening 26 when the detector device is not in use.

Bottom neck portion 14 includes a hollow tubular element 32 having a plastic flap valve 34 connected thereto by a plastic hinge means 36. The valve 34 closes the opening 33 at the upper end of element 32, the opening 33 serving as the container inlet port. A stopper 38 is provided on a cap member 40 for closing the lower opening of element 32 when the detector device is not in use. Cap member 40 is hingedly connected to the neck portion 14 by a plastic hinge means in a manner known in the art.

The container 10 is provided with a fiducial line or mark 42 which indicates the level to which the container should be filled with liquid. If the device is to be used as a gas detector, then the liquid 20 should be a liquid which changes color upon coming in contact with the particular gas being detected. Therefore, the container 10 should be made of a transparent plastic material which will permit viewing of the color of the liquid 20 from the exterior of the container. As used herein, the term transparent is intended to include translucent materials which will also permit the color of the liquid to be determined from the outside of the container.

To use the device as a gas detetor, stopper members 30 and 38 are opened and the container 10 is filled through the bottom inlet port 33 with detecting liquid 20 up to the fill level 42. This may be accomplished by inserting neck 14 into a container holding the liquid, and successively squeezing and releasing the sides of the container 10 until enough liquid is drawn into container 10 to fill it to the fill mark 42. Each squeeze of container 10 will exhaust air from the container 10 through outlet port 23, and each time the container is released it will return to its normal configuration thus drawing liquid in through port 33. The particular gas being detected will determine exactly which liquid 20 should be utilized in the container. For example, if carbon monoxide is to be detected, then the liquid 20 may be a solution of Bromo Cresol Green and water.

After the liquid 20 has been placed in the container 10 the device is ready for use as a gas detector. The user repeatedly squeezes and then releases the container 10 so that the pressure within container 10 repeatedly changes from some value above atmospheric pressure to some value below atmospheric pressure. As the container 10 is squeezed, the pressure within the container becomes greater than the ambient pressure, thereby opening valve 22 and exhausting into the atmosphere gases contained in container 10 above the level of the fluid 20. Each time the container 10 is released, it expands back to its original shape and the pressure within the container drops below atmospheric pressure. The higher atmospheric pressure forces inlet valve 34 open and the ambient atmosphere bubbles up through liquid 20.

After this cycle of operation has been repeated several times, a sufficient quantity of the atmospheric gases will have been bubbled through liquid 20 for the liquid to give an indication of whether or not a specified gas being tested for is present in the atmosphere. If the gas being tested for is present, then the liquid 20 changes color and this will be evident by viewing the liquid through the container 10. If the liquid 20 does not change color, then the user knows that the gas being tested for is not present in the ambient atmosphere.

If the liquid 20 is Bromo Cresol Green and the gas being tested for is carbon monoxide, then it is not necessary to replace the liquid 20 after each test. Bromo Cresol Green has the property that it returns to its original color if air is bubbled therethrough which does not contain carbon monoxide. Thus, after a test is made, the user may transport the container 10 to an atmosphere not contaminated with carbon monoxide and then squeeze and release the container 10 several times to bubble air through the liquid 20. This will restore the Bromo Cresol Green to its original color.

When the device is not in use, the stopper 30 is inserted into the opening 26 and the stopper 38 is inserted into the opening 44 at the lower end of cap portion 14. This completely seals the container and prevents loss of the fluid.

Should a user wish to empty the detector liquid from container 10, this can be accomplished by holding the container in an upright position, inserting a toothpick or other small probe into opening 44 and gently lifting valve 34 while applying pressure to the sides of the container. The container may be rinsed by filling it with water or another rinsing liquid using the filling procedure described above.

Although the invention has been described specifically in connection with the detection of carbon monoxide, it may be used to test for other gases or even test for the presence of solid particles floating in the atmosphere. All that is required is that the proper detecting liquid 20 be utilized in the device.

Furthermore, the device illustrated in FIG. 1 may be utilized as a vaporizer. The only difference is that the liquid to be vaporized and ejected into the atmosphere is used as the liquid 20. As air is bubbled up through the liquid, a small amount of the liquid is vaporized and passes into the region 46 above the liquid level. Each time the bottom is squeezed, this vapor is then ejected through the outlet port 23 into the atmosphere.

From the foregoing description, it is seen that the present invention provides a very simple gas detector or vaporizor which is inexpensive and which can be operated by one having no special tedchnical skills. All the elements thereof, except for the liquid, may be made of plastic materials. It is portable and is extremely easy to use.

While a preferred embodiment of the invention has been described in specific detail, it will be understood that various substitutions, additions, and modifications may be made therein without departing from the spirit and scope of the invention as defined by the appended claims.

The embodiments of the invention in which an exclusive property or privilege is claimed are defined as follows:

I claim:
1. A test device comprising:
   a transparent container means for holding detector liquid in a cavity thereof, the container means being flexible and resilient whereby it may be squeezed and released to alternately decrease and increase the volume of its cavity, said container means further defining inlet and outlet ports therein;

an inlet oneway valve means positioned at said inlet port for covering said inlet port and contacting said detector liquid in said cavity when said container means is oriented with said inlet port directed downwardly to prevent said detector liquid from passing out through said inlet port in response to pressure inside the cavity but for moving from said port to allow fluid to enter through said inlet port and pass through said detector liquid in response to a negative pressure inside the cavity;

an outlet assembly positioned at said outlet port, said outlet assembly comprising an outlet one-way valve means positioned at said outlet port for covering said outlet port and for contacting fluid outside said cavity to prevent said fluid outside said cavity from entering said cavity in response to a negative pressure inside said cavity, but for allowing fluid inside said cavity to pass through said port in response to a positive pressure inside said cavity, said outlet assembly further comprising a tube extending into said cavity from said outlet port for forming a tube opening to said outlet one-way valve from said cavity above an upper surface of said detector liquid when said container means is oriented with said outlet port directed either downwardly or upwardly to prevent said detector liquid from contacting said one-way valve means and passing out through said outlet port;

the volumes of portions of said cavity, external of said tube, both above and below said tube opening when said outlet valve means is directed upwardly, each being sufficiently great that an identical volume of detector liquid when in said cavity, contacts and covers said inlet one-way valve means when said inlet one-way valve means is directed downwardly;

said detector liquid being a liquid which changes color upon being brought into contact with a specified substance.

2. A device as claimed in claim 1 wherein said inlet and outlet one-way valve means are plastic flap valves, and plastic hinge means hingedly connecting said valves to said container.

3. A device as claimed in claim 1 wherein said inlet and outlet one-way valve means are plastic flap valves.

4. A device as claimed in claim 1 wherein said container has first and second neck portions located at the top and bottom of said container when it is in position for use, said inlet and outlet one-way valve means being located in said bottom and said top neck portions, respectively.

5. A test device comprising:

a container means for holding detector liquid in a cavity thereof, the container means being flexible and resilient whereby it may be squeezed and released to alternately decrease and increase the volume of its cavity, said container means further defining inlet and outlet ports therein;

an inlet one-way valve means positioned at said inlet port for covering said inlet port and contacting said detector liquid in said cavity when said container means is oriented with said inlet port directed downwardly to prevent said detector liquid from passing out through said inlet port in response to pressure inside the cavity but for moving from said port to allow fluid to enter through said inlet port and pass through said detector liquid in response to a negative pressure inside the cavity;

an outlet assembly positioned at said outlet port, said outlet assembly comprising an outlet one-way valve means positioned at said outlet port for covering said outlet port and for contacting fluid outside said cavity to prevent said fluid outside said cavity from entering said cavity in response to a negative pressure inside said cavity, but for allowing fluid inside said cavity to pass through said port in response to a positive pressure inside said cavity, said outlet assembly further comprising a tube extending into said cavity from said outlet port for forming a tube opening to said outlet one-way valve from said cavity above an upper surface of said detector liquid when said container means is oriented with said outlet port directed either downwardly or upwardly to prevent said detector liquid from contacting said one-way valve means and passing out through said outlet port;

the volumes of portions of said cavity, external of said tube, both above and below said tube opening when said outlet valve means is directed upwardly, each being sufficiently great that an identical volume of detector liquid when in said cavity, contacts said inlet one-way valve means when said inlet one-way valve means is directed downwardly.

6. A device as claimed in claim 5 wherein said liquid is a detector liquid which changes color upon being brought into contact with a specified substance, said container being made of a transparent plastic material whereby the color of said liquid may be viewed from the exterior of said container.

7. A device as claimed in claim 5 wherein said liquid is Bromo Cresol Green which changes color upon being brought into contact with a specified substance, said container being made of a transparent plastic material whereby the color of said liquid may be viewed from the exterior of said container.

8. A test device comprising:

a container holding a detector liquid therein, said container being flexible and resilient whereby it may be alternately squeezed and released to alternately decrease and increase its internal volume;

means defining inlet and outlet ports into and out of said container, said outlet port being located above the level of said liquid and said inlet port being located below the top surface of said liquid when said container is positioned ready for use and is partially filled with said detector liquid; and, inlet and outlet valves for controlling said inlet and outlet ports respectively in response to variations in the relative pressures within and without said container, the pressure without said container being ambient atmospheric pressure;

said pressures within and without said container acting on said inlet and outlet valves to open said inlet valve and close said outlet valve when the pressure within said container is less than the pressure without, and to close said inlet valve and open said outlet valve when the pressure within the container is greater than the pressure without, whereby ambient atmospheric gases are drawn into said container through said inlet valve and passed through said detector liquid, and only gas is expelled from said outlet valve;

said container defining an interior volume and said device further including a hollow tube extending through a wall of said container and terminating at one end at an opening above the level of said liquid near a central portion of said interior volume of said container, and said hollow tube having a second end, said outlet port being located at said second end of said tube.

* * * * *